(12) United States Patent
King et al.

(10) Patent No.: US 6,489,499 B1
(45) Date of Patent: Dec. 3, 2002

(54) SILOXANE MODIFIED CARBOXYLIC ACID SUBSTITUTED AMINES AND SALTS THEREOF

(75) Inventors: Wayne King, Levittown, PA (US); John H. MacMillan, Ambler, PA (US); Michael J. Telepchak, Yardley, PA (US)

(73) Assignee: United Chemical Technologies, Inc., Bristol, PA (US)

( * ) Notice: Subject to any disclaimer, the term of this patent is extended or adjusted under 35 U.S.C. 154(b) by 0 days.

(21) Appl. No.: 10/096,047

(22) Filed: Mar. 11, 2002

(51) Int. Cl.[7] .................................................. C07F 7/10
(52) U.S. Cl. ....................... 556/413; 556/400; 556/418; 556/424; 556/437; 556/438; 556/440
(58) Field of Search ................................ 556/413, 418, 556/400, 437, 438, 440, 424

(56) References Cited

U.S. PATENT DOCUMENTS

| | | | | |
|---|---|---|---|---|
| 5,399,653 A | * | 3/1995 | Lucarelli et al. | ............. 556/418 |
| 5,516,869 A | * | 5/1996 | Lucarelli et al. | ............. 556/418 |
| 6,251,595 B1 | | 6/2001 | Gordon et al. | |
| 6,319,674 B1 | | 11/2001 | Fulcrand et al. | |
| 6,379,751 B1 | * | 4/2002 | Schafer et al. | ............... 556/418 |

* cited by examiner

*Primary Examiner*—Paul F. Shaver
(74) *Attorney, Agent, or Firm*—Robert A. Koons Jr., Esq.; Matthew P. McWilliams; Buchanan Ingersoll, P.C.

(57) ABSTRACT

Novel compounds comprising siloxane modified carboxylic acid substituted amines and salts thereof are provided. The compounds according to the invention provide many of the desirable properties of ethylenediamine tetraacetic acid and its salts in a stationary phase. A process for synthesis of the compounds according to the invention are also provided.

47 Claims, No Drawings

SILOXANE MODIFIED CARBOXYLIC ACID SUBSTITUTED AMINES AND SALTS THEREOF

FIELD OF THE INVENTION

The present invention is drawn generally to the field of acid modified amines for use as chelating agents and coatings. More specifically, the present invention is drawn to siloxane modified derivatives of carboxylic acid substituted amines and the salts thereof.

BACKGROUND OF THE INVENTION

Ethylenediamine tetraacetic acid (EDTA) and its salts are well known. Ethylenediamine tetraacetic acid is widely employed as a chelating agent for a variety of metal ions. Also, EDTA is quite polar and a rich source of active carboxylic acid functionality. However, EDTA by itself is incapable of bonding to a substrate surface without disrupting the acid functionality necessary for effective chelation.

If an EDTA like moiety, i.e. a carboxylic acid substituted alkyl amine, could be bonded covalently to a substrate surface, it would be possible to take advantage of a number of the beneficial properties of EDTA in a stationary phase. Further, a substrate surface coated with such a compound or a salt thereof would be extremely hydrophilic and wettable. It is therefore desirable to generate functionalized EDTA like compounds that allow chemical interactions with the substrate surface without affecting the acid groups.

SUMMARY OF THE INVENTION

The present invention provides novel compounds comprising siloxane modified amines that are substituted with one or more carboxylic acids having 1 to 20 carbon atoms. The compounds may also be prepared as salts using one or more appropriate metal hydroxides. The present invention further provides a method of synthesizing such compounds. Such compounds can be bonded to a number of substrates in a known way to produce a stationary phase having many of the beneficial properties of EDTA and salts thereof.

The novel compounds according to the current invention have a general structure selected from:

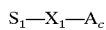  I and

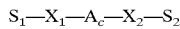  II wherein, $S_1$ and $S_2$ are independently a mono, di or tri siloxane, $X_1$ and $X_2$ are independently alkyl, alkenyl or aryl having from 1 to 20 carbon atoms, and $A_c$ is a carboxylic acid substituted amine or a salt thereof.

Siloxane coupling agents are widely known as affective reagents to couple a functional group to a polar substrate such as glass, silica, quartz, inorganic metal oxides, thoria, silicon, alumina, aluminum, iron, zinc, corona or plasma treated plastics and hydroxy functionalized plastics. These siloxane coupling reagents possess one or more alkoxysilyl groups at one end of the molecule and the active functional group at the other end of the molecule. On hydrolysis in aqueous media the alkoxysilyl groups hydrolyze to active silanol groups. These silanol groups readily form covalent bonds to polar substrates. The substrate surface is then functionalized with the active group at the other end of the siloxane molecule. These siloxane coupling agents as both the free alkoxysilyl and bound to the substrate are referred to herein as siloxanes. Siloxanes that are useful according to the current invention have a general structure selected from:

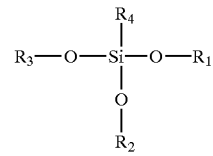  I

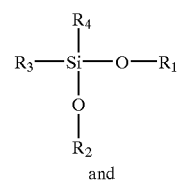  II and

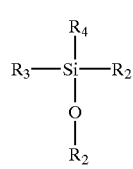  III wherein, $R_1$, $R_2$ and $R_3$ are independently alkyl, alkenyl, aryl or a substrate, and $R_4$ is either $X_1$ or $X_2$, provided that when $R_1$ is bound directly to Si, it is not a substrate and when $R_3$ is bound directly to Si, it is not a substrate. The two embodiments shown provide one or two siloxane functional groups for binding the carboxylic acid modified amine to a substrate. However, it is possible to provide additional siloxane groups as bonding sites.

Further, the amine portion is preferably selected from mono, di, tri and tetra amines having a general structure selected from:

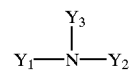  I

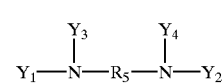  II

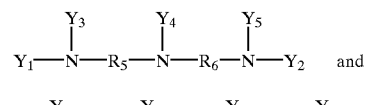  III and

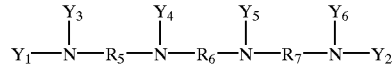  IV wherein, $Y_1$ and $Y_2$ are independently $X_1$, $X_2$ or a carboxylic acid or salt thereof having from 1 to 20 carbon atoms, $Y_3$, $Y_4$, $Y_5$ and $Y_6$ are independently a carboxylic acid or salt thereof having from 1 to 20 carbon atoms, and $R_5$, $R_6$ and $R_7$ are independently alkyl, alkenyl or aryl, provided that at least one of $Y_1$ and $Y_2$ is either $X_1$ or $X_2$. In the embodiment where both of $Y_1$ and $Y_2$ are either $X_1$ or $X_2$ the compound is provided with two siloxane bonding sites.

The novel compounds according to the current invention may be synthesized from the corresponding siloxane modified amines having the general structures:

  I and

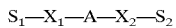  II wherein, $S_1$ and $S_2$ are independently a mono, di or tri siloxane, $X_1$ and $X_2$ are independently alkyl, alkenyl or aryl having from 1 to 20 carbon atoms, and A is an amine. A solution is prepared of at least one halogenated carboxylic acid having from 1 to 20 carbon atoms. The siloxane modified amine is then added to the solution in a metered fashion. Preferably the halogenated carboxylic acid is added as an aqueous solution. A suitable metal hydroxide may then be added to the combined mixture or solution to generate a metal salt of the carboxylic acid modified amine. The amine is preferably an un-substituted mono, di, tri or tetra amine having a structure selected from:

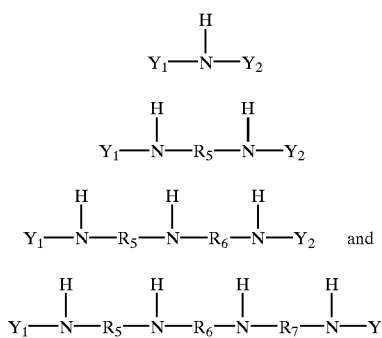

wherein, $Y_1$ and $Y_2$ are independently $X_1$, $X_2$ or hydrogen, $R_5$, $R_6$ and $R_7$ are independently alkyl, alkenyl or aryl, and H is hydrogen, provided that at least one of $Y_1$ and $Y_2$ is either $X_1$ or $X_2$.

The siloxane modified carboxylic acid substituted amines according to the current invention can be applied to a number of different substrate surfaces to generate a modified substrate surface. Such modified substrate surfaces have a number of different applications in medical diagnostics, chemical synthesis and analytical chemistry, DNA and Protein immobilization, and metal chelation as well as in the field of electronics. Particularly, application of a salt, preferably a metal salt, of a siloxane modified carboxylic acid substituted amine according to the current invention provides a modified substrate surface that is extremely wettable compared to an unmodified substrate surface. Such properties are very desirable in the electronics industry. The preferred salt for this application is the potassium salt. Although a number of salts effectively produce a wettable surface, the low levels of sodium required for electronics applications make the potassium salt preferable.

DETAILED DESCRIPTION OF THE INVENTION

The novel siloxane modified carboxylic acid substituted amines according to the current invention are produced from the corresponding un-substituted siloxane modified amines. Exemplary amines of this type, available from United Chemical Technologies, Inc., are shown in Table 1.

TABLE 1

| | | |
|---|---|---|
| 1. | (Aminoethylaminomethyl)phenyl tri-methoxysilane | 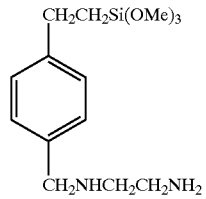 |
| 2. | N-(2-Aminoethyl)-3-aminopropylmethyl dimethoxysilane | 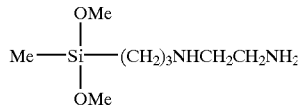 |
| 3. | N-(2-Aminoethyl)-3-aminopropyl trimethoxysilane | 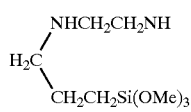 |
| 4. | N-2-(Aminoethyl)-3-aminopropyl tris(2-ethyl-hexoxy)silane | 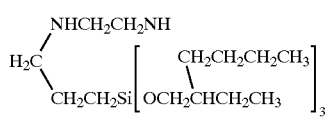 |
| 5. | Trimethoxysilylpropyl diethylenetriamine | 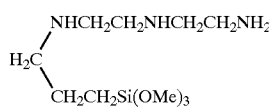 |
| 6. | N-(6-Aminohexyl)aminopropyl triemthoxysilane | 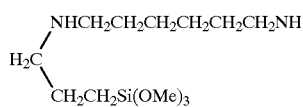 |
| 7. | 3-(1-Aminopropoxy-3,3-dimethyl-1-propenyl trimethoxysilane | 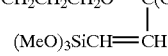 |

TABLE 1-continued 8. 3-Aminopropyltris(methoxyethoxy)silane $$Si(OCH_2CH_2OCH_2CH_2OMe)_3$$
$$|$$
$$CH_2CH_2CH_2NH_2$$

9. 3-Aminopropyldimethoxysilane $$H_2NCH_2CH_2CH_2-\underset{\underset{Me}{|}}{\overset{\overset{Me}{|}}{Si}}OEt$$

10. 3-Aminopropylmethyldiethoxysilane $$H_2NCH_2CH_2CH_2-\underset{\underset{OEt}{|}}{\overset{\overset{OEt}{|}}{Si}}Me$$

11. 3-Aminopropyldiisopropylethoxysilane $$H_2NCH_2CH_2CH_2-\underset{\underset{CH(CH_3)_2}{|}}{\overset{\overset{CH(CH_3)_2}{|}}{Si}}OEt$$

12. Trimethoxysilylpropyl modified Polyethylene Imine

—NCH₂CH₂NCH₂CH₂NCH₂CH₂N—
with (CH₂)₃ branches to Si(OMe)₃ groups

13. Dimethoxymethylsilylpropyl Substituted Polyethylene Imine

—NCH₂CH₂NCH₂CH₂NCH₂CH₂N—
with (CH₂)₃ branches to Si(OMe)₂Me groups

As shown in Table 1, suitable siloxane modified amines may be polyamines. Preferred amines are mono, di, tri and tetra. Further suitable starting materials may contain straight or branched alkanes, as well as, un-saturated elements, including aryl moieties. Additionally, polymeric materials such as examples 12 and 13 from Table 1 may be substituted with carboxylic acids according to the current invention. In addition, alkyl amines that are already bonded to a substrate may be substituted with halogenated carboxylic acids according to the current invention. Examples of such materials that are available from United Chemical Technologies, Inc include aminoethyl and aminopropyl modified silicas.

The siloxane portion of the starting material may be a mono, di or tri siloxane. Further, it may be alkoxy, alkenoxy, aryloxy or a combination thereof. Preferred siloxanes are the methoxy and ethoxy, more preferably the trimethoxy or triethoxy. However, the only requirement is that the siloxane be capable of being hydrolyzed to produce the requisite silanol for bonding to a substrate surface. In one embodiment, the modified amine may be supplied already bound to a substrate surface, such as the exemplary silica supported amines.

The siloxane modified carboxylic acid substituted amines according to the current invention are produced by reaction with the desired halogenated carboxylic acid or mixture of acids. The halogenated acids may be any of fluoro, chloro, bromo or iodo. Preferably, the halogenated acid is provided as a solution in a suitable solvent. More preferably, the halogenated acid is provided as an aqueous solution. In the case that the un-substituted amine is supported on a substrate, it may be provided as a mixture or immersed in water or other suitable solvent. The aqueous carboxylic acid solution may be heated as necessary to achieve complete dissolution of the acid. The un-substituted amine is then added to the agitated halogenated acid in a metered fashion to control the exothermic reaction. Care must be taken in the heating of the acid and addition of the un-substituted amine to ensure that the product does not decompose. Any halogenated carboxylic acid having from 1 to 20 carbon atoms may be used according to the process of the current invention. Preferred acids for the process are chloroacetic acid, bromoacetic acid, iodoacetic acid, 1-chloropropionic acid, 2-chloropropionic acid, 1-bromopropionic acid, 2-bromopropionic acid, and 1-iodopropionic acid and 2-iodopropionic acid. The solution is then allowed to cool under agitation.

A salt of the siloxane modified carboxylic acid substituted amine may be prepared by addition of an appropriate metal hydroxide to the above siloxane modified carboxylic acid substituted amine. A solution of a single metal hydroxide or mixture of several metal hydroxides is prepared and metered into an agitated solution or mixture of the siloxane modified carboxylic acid substituted amine. The addition is preferably done in such a way to maintain the temperature of the reaction mass below about 50° C. Preferably, the reaction medium is aqueous. Any waste metal salts, such as sodium or potassium halides that are formed by this process readily precipitate on cooling of the product solution and can be removed by filtration. Suitable metal hydroxides for forming the metal salt include but are not limited to: lithium, sodium, potassium, cesium, barium, magnesium, calcium and strontium.

EXAMPLE 1

A solution was prepared of 2 kilograms of chloroacetic acid and 1.64 kilograms deionized water in a 12 L flask. An addition funnel was charged with 1.56 kilograms of a siloxane modified un-substituted amine, N-(2-aminoethyl)-3-aminopropyltrimethoxysilane, available from United Chemical Technologies, Inc. as catalogue number A0700. The N-(2-aminoethyl)-3-aminopropyltrimethoxysilane was added to the chloroacetic acid solution with stirring. The addition was performed at a rate to keep the temperature of the reaction mass below 60° C. After the addition, the reaction mass was stirred for 2 hours and left to cool to room temperature. A solution was prepared of about 50 mole percent potassium hydroxide by adding 2.36 kilograms potassium hydroxide to 1.65 kilograms deionized water. The potassium hydroxide solution was added through an addition funnel at a rate to keep the temperature of the reaction mass below 50° C. Following the addition the reaction mass was left to cool to room temperature with agitation.

A typical run thus prepared results in a 52.53 weight percent solution of the siloxane modified amine tricarboxylic acid tripotassium salt, based on analysis by titration with a standard perchloric acid solution.

EXAMPLE 2

The procedure as described in Example 1 was carried out with the exception that in place of potassium hydroxide, sodium hydroxide was used to form the acid salt. A solution was prepared of 50% sodium hydroxide by adding 1.68 kilograms sodium hydroxide to 1.65 kilograms deionized water. The 50% sodium hydroxide solution was added through an addition funnel at a rate to keep the temperature of the reaction mass below 50° C. Following the addition the reaction mass was left to cool to room temperature with agitation.

A typical run thus prepared results in a 49.1 weight percent solution of the siloxane modified amine tricarboxylic acid trisodium salt, based on analysis by titration with a standard perchloric acid solution.

The reaction as carried out in Examples 1 and 2 provides a siloxane modified ethylenediaminetriacetic acid metal salt, which has the structure:

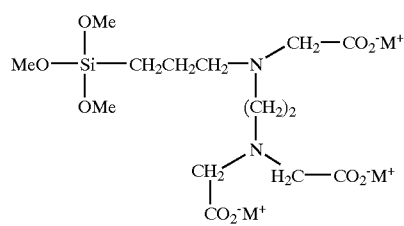

wherein M is potassium or sodium. It will be recognized that other salts, such as lithium, cesium, barium, magnesium, calcium, strontium or mixtures of salts may be prepared by utilizing the appropriate metal hydroxide or hydroxides.

As can be seen from the siloxane modified ethylenediamine triacetic acid in the example, the siloxane modified carboxylic acid substituted amines have a structure very similar to ethylenediamine tetraacetic acid (EDTA). Thus these compounds possess many of the same desirable properties as EDTA, as well as the added benefit of being capable of bonding to a substrate surface. The siloxane modified carboxylic acid substituted amines of the current invention can be bonded to any substrate possessing the requisite surface hydroxyl groups. Suitable substrates include, but are not limited to: generic glass, borosilicate glass, soda lime glass, quartz, silica, alumina, thoria, zeolites, inorganic clays, inorganic metal oxides, diatomaceous earth, activated plastics, corona treated plastics, plasma treated plastics, hydroxyl functional plastics, T-resins, silsesquioxanes, sol gels, organosils, activated silicones, plasma treated silicones, corona treated silicones, activated polydimethylsilanes, plasma treated polydimethylsilanes, corona treated polydimethylsilanes and inorganic metal oxides. The substrate may also be a metal such as aluminum, silicon, iron, steel, zinc, nickel, tin, magnesium, titanium, cobalt, chromium or an alloy of two or more.

Because the siloxane modified carboxylic acid substituted amines according to the current invention possess many of the same properties of EDTA, when bound to a substrate surface, they have a number of different applications, including but not limited to medical diagnostics, chemical synthesis and analytical chemistry, DNA and Protein immobilization, and metal chelation, as well as in the field of electronics. Of particular interest in the field of electronics is providing a wettable modified surface. Salts of the siloxane modified carboxylic acid substituted amines according to the current invention provide an extremely wettable surface when bound to a substrate surface compared to an unmodified substrate surface.

EXAMPLE 3

Four grams of an approximately 50 weight percent solution of the tripotassium salt of the siloxane modified ethylene diamine triacetic acid produced according to Example 1 was dissolved in 96 g water in a 250 ml beaker, generating a 2 weight percent solution of the salt. A standard soda lime glass microscope slide was immersed in this solution for 15 minutes. The slide was removed from the solution, washed with distilled water, and cured at room temperature for twenty four hours. Comparison of the contact angle of the treated glass slide with that for an untreated glass slide was performed qualitatively by placing a drop of water on both. The treated slide showed greater wetting of the water drop compared to the untreated slide, indicative of bonding of the polar siloxane modified ethylene diamine triacetic acid tripotassium salt derivative to the glass.

The preceding examples have been provided to demonstrate the utility of the compounds and process of the current invention and are in no way intended to limit the scope of the present invention. Those skilled in the art will recognize that the siloxane modified amines that can be substituted with carboxylic acids using the method of the current invention are not limited to the several examples provided.

What is claimed is:

1. A composition comprising a silane modified carboxylic acid substituted amine or a salt thereof, having a general structure selected from:

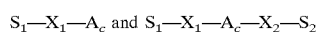

wherein, $X_1$ and $X_2$ are independently alkyl, alkenyl or aryl, and $A_c$ is a carboxylic acid substituted amine or a salt thereof, and $S_1$ and $S_2$ independently have structures selected from,

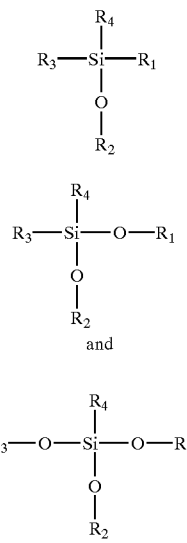

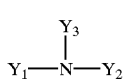

wherein, $R_1$, $R_2$ and $R_3$ are independently alkyl, alkenyl, aryl, hydrogen or a substrate, and $R_4$ is either $X_1$ or $X_2$, provided that when $R_1$ is bound directly to Si, $R_1$ is not a substrate and when $R_3$ is bound directly to Si, $R_3$ is not a substrate.

2. The composition of claim 1, wherein said amine is an alkyldiamine.

3. The composition of claim 2, wherein said alkyldiamine is ethylenediamine.

4. The composition of claim 1, wherein said amine is an alkyltriamine.

5. The composition of claim 1, wherein said amine is an alkyltetraamine.

6. The composition of claim 1, wherein said amine is incorporated into a polymer.

7. The composition of claim 1, wherein said substrate is selected from the group consisting of: generic glass, borosilicate glass, soda lime glass, quartz, silica, alumina, thoria, zeolites, inorganic clays, diatomaceous earth, activated plastics, corona treated plastics, plasma treated plastics, hydroxyl functional plastics, T-resins, silsesquioxanes, sol gels, organosils, activated silicones, plasma treated silicones, corona treated silicones, activated polydimethylsilanes, plasma treated polydimethylsilanes, corona treated polydimethylsilanes and inorganic metal oxides.

8. The composition of claim 1, wherein said substrate is a metal selected from the group consisting of: aluminum, silicon, iron, steel, zinc, nickel, tin, magnesium, titanium, cobalt, chromium and alloys thereof.

9. The composition of claim 1, wherein said salt is a metal salt selected from at least one of the group consisting of: lithium, sodium, potassium, cesium, barium, magnesium, calcium and strontium.

10. The composition of claim 1, wherein said carboxylic acid substituted amine or salt thereof has a structure selected from:

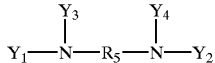

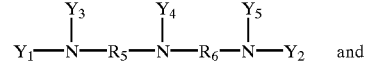

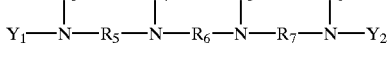

wherein, $Y_1$ and $Y_2$ are independently $X_1$, $X_2$ or a carboxylic acid or salt thereof having from 1 to 20 carbon atoms, $Y_3$, $Y_4$, $Y_5$ and $Y_6$ are independently a carboxylic acid or salt thereof having from 1 to 20 carbon atoms, and $R_5$, $R_6$ and $R_7$ are independently alkyl, alkenyl or aryl, provided that at least one of $Y_1$ and $Y_2$ is either $X_1$ or $X_2$.

11. The composition of claim 10, wherein, $R_5$, $R_6$ and $R_7$ are all ethylene and said carboxylic acid is selected from the group consisting of: acetic acid and propionic acid.

12. The composition of claim 10, wherein said substrate is selected from the group consisting of: generic glass, borosilicate glass, soda lime glass, quartz, silica, alumina, thoria, zeolites, inorganic clays, diatomaceous earth, activated plastics, corona treated plastics, plasma treated plastics and hydroxyl functional plastics, T-resins, silsesquioxanes, sol gels, organosils, activated silicones, plasma treated silicones, corona treated silicones, activated polydimethylsilanes, plasma treated polydimethylsilanes and corona treated polydimethylsilanes.

13. The composition of claim 10, wherein said substrate is a metal selected from the group consisting of: aluminum, silicon, iron, steel, zinc, nickel, tin, magnesium, titanium, cobalt, chromium and alloys thereof.

14. The composition of claim 10, wherein $S_1$ and $S_2$ are selected from the group consisting of trimethoxy silane and triethoxy silane.

15. The composition of claim 12, wherein, $R_5$, $R_6$ and $R_7$ are all ethylene and said carboxylic acid or salt thereof is selected from the group consisting of acetic and propionic.

16. The composition of claim 13, wherein, $R_5$, $R_6$ and $R_7$ are all ethylene and said carboxylic acid or salt thereof is selected from the group consisting of acetic and propionic.

17. The composition of claim 14, wherein, $R_5$, $R_6$ and $R_7$ are all ethylene and said carboxylic acid or salt thereof is selected from the group consisting of acetic and propionic.

18. The composition of claim 10, wherein said salt is a metal salt selected from at least one the group consisting of: lithium, sodium, potassium, cesium, barium, magnesium, calcium and strontium.

19. The composition according to claim 14, wherein said salt is the potassium salt.

20. The composition according to claim 14, wherein said salt is the potassium salt.

21. The composition according to claim 16, wherein said salt is the potassium salt.

22. A method of preparing a silane modified carboxylic acid substituted amine or a salt thereof, said method comprising a) providing a composition comprising a silane modified amine having a structure selected from:

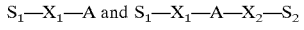

wherein, $X_1$ and $X_2$ are independently alkyl, alkenyl or aryl, $S_1$ and $S_2$ independently have structures selected from,

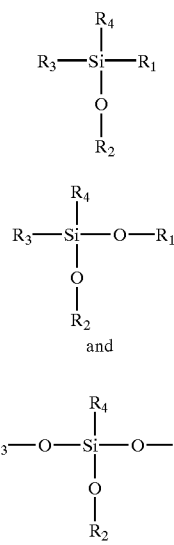

wherein, $R_1$, $R_2$ and $R_3$ are independently alkyl, alkenyl, aryl, hydrogen or a substrate, and $R_4$ is either $X_1$ or $X_2$, provided that when $R_1$ is bound directly to Si, $R_1$ is not a substrate and when $R_3$ is bound directly to Si, $R_3$ is not a substrate, and A is an amine;
b) reacting said composition, with at least one halogenated carboxylic acid having from 1 to 20 carbon atoms; and
c) adding to said composition, at least one metal hydroxide.

23. The method according to claim 22, wherein said halogenated carboxylic acid and said at least one metal hydroxide comprise aqueous solutions.

24. The method according to claim 23, wherein said halogenated carboxylic acid solution is heated to a temperature less than about 60° C.

25. The method according to claim 23, wherein said adding of said metal hydroxide solution is performed such that the temperature of the combined mixture is maintained at or below about 50° C.

26. The method of claim 22, wherein said amine has a structure selected from:

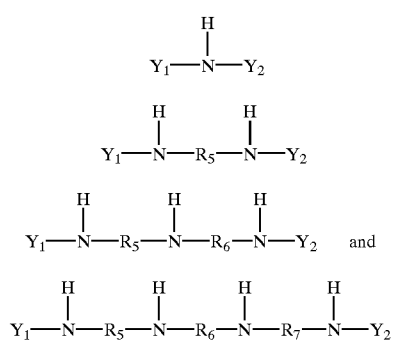

wherein, $Y_1$ and $Y_2$ are independently $X_1$, $X_2$ or hydrogen, $R_5$, $R_6$ and $R_7$ are independently alkyl, alkenyl or aryl, and H is hydrogen, provided that at least one of $Y_1$ and $Y_2$ is either $X_1$ or $X_2$.

27. The method according to claim 26, wherein said at least one halogenated carboxylic acid is selected from the group consisting of chloroacetic acid, bromoacetic acid, iodoacetic acid, 1-chloropropionic acid, 2-chloropropionic acid, 1-bromopropionic acid, 2-bromopropionic acid, and 1-iodopropionic acid and 2-iodopropionic acid.

28. The method according to claims 26, wherein said at least one metal hydroxide is selected from the group consisting of: lithium, sodium, potassium, cesium, barium, magnesium, calcium and strontium.

29. A method for producing a modified surface, said method comprising:

providing a surface to be modified,
providing an aqueous solution comprising a silane modified carboxylic acid substituted amine or a salt thereof, having a general structure selected from:

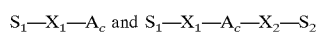

wherein, $X_1$ and $X_2$ are independently alkyl, alkenyl or aryl, $S_1$ and $S_2$ independently have structures selected from,

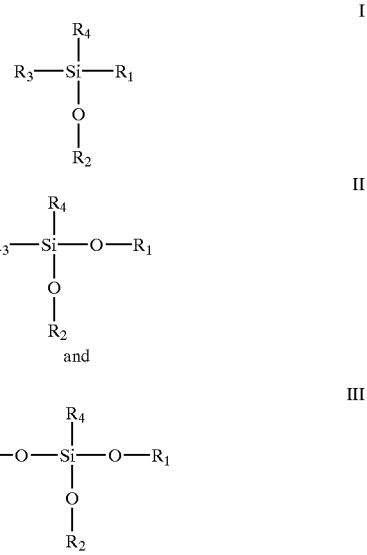

wherein, $R_1$, $R_2$ and $R_3$ are independently alkyl, alkenyl or aryl, and $R_4$ is either $X_1$ or $X_2$, and $A_c$ is a carboxylic acid substituted amine or a salt thereof, hydrolyzing said silane modified carboxylic acid substituted amine or salt thereof to generate at least one Si—O—H, applying said solution to said surface, and
curing said surface.

30. The method of claim 29, wherein said carboxylic acid substituted amine or salt thereof has a structure selected from:

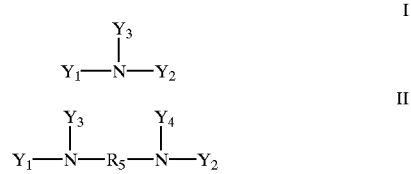

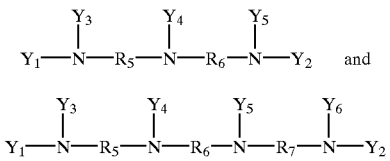

wherein, $Y_1$ and $Y_2$ are independently $X_1$, $X_2$ or a carboxylic acid or salt thereof having from 1 to 20 carbon atoms, $Y_3$, $Y_4$, $Y_5$ and $Y_6$ are independently a carboxylic acid or salt thereof having from 1 to 20 carbon atoms, and $R_5$, $R_6$ and $R_7$ are independently alkyl, alkenyl or aryl, provided that at least one of $Y_1$ and $Y_2$ is either $X_1$ or $X_2$.

31. The method of claim 29, wherein said surface is a substrate selected from the group consisting of: generic glass, borosilicate glass, soda lime glass, quartz, silica, alumina, thoria, zeolites, inorganic clays, diatomaceous earth, activated plastics, corona treated plastics, plasma treated plastics, hydroxyl functional plastics, T-resins, silsesquioxanes, sol gels, organosils, activated silicones, plasma treated silicones, corona treated silicones, activated polydimethylsilanes, plasma treated polydimethylsilanes and corona treated polydimethylsilanes.

32. The method of claim 29, wherein said surface is a metal selected from the group consisting of: aluminum, silicon, iron, steel, zinc, nickel, tin, magnesium, titanium, cobalt, chromium and alloys thereof.

33. The method of claims 31, wherein, $R_5$, $R_6$ and $R_7$ are all ethylene and said carboxylic acid or salt thereof is selected from the group consisting of acetic and propionic.

34. The method of claim 32, wherein, $R_5$, $R_6$ and $R_7$ are all ethylene and said carboxylic acid or salt thereof is selected from the group consisting of acetic and propionic.

35. The method according to claim 29, wherein said salt is at least one metal salt selected from the group consisting of: lithium, sodium, potassium, cesium, barium, magnesium, calcium and strontium.

36. The method of claim 33, wherein said salt is the potassium salt.

37. The method of claim 34, wherein said salt is the potassium salt.

38. The method of claim 36, wherein $S_1$ and $S_2$ are selected from the group consisting of trimethoxy silane and triethoxy silane.

39. The method of claim 37, wherein $S_1$ and $S_2$ are selected from the group consisting of trimethoxy silane and triethoxy silane.

40. The method of claim 30, wherein said surface is made wettable.

41. The method of claim 40, wherein said surface is silicon.

42. The method of claim 41, wherein, $R_5$, $R_6$ and $R_7$ are all ethylene and said carboxylic acid or salt thereof is selected from the group consisting of acetic and propionic.

43. The method of claim 42, wherein said salt is the potassium salt.

44. The method of claim 43, wherein $S_1$ and $S_2$ are selected from the group consisting of trimethoxy silane and triethoxy silane.

45. The composition according to claim 1, wherein at least one of $R_1$, $R_2$, $R_3$ and $R_4$ contain at least one heteroatom.

46. The method according to claim 22, wherein at least one of $R_1$, $R_2$, $R_3$ and $R_4$ contain at least one heteroatom.

47. The method according to claim 29, wherein at least one of $R_1$, $R_2$, $R_3$ and $R_4$ contain at least one heteroatom.

* * * * *

UNITED STATES PATENT AND TRADEMARK OFFICE
CERTIFICATE OF CORRECTION

PATENT NO.    : 6,489,499 B1
DATED         : December 3, 2002
INVENTOR(S)   : King et al.

It is certified that error appears in the above-identified patent and that said Letters Patent is hereby corrected as shown below:

Title page, Item [54] and Column 1, line 1,
Title, delete "SILOXANE" and insert -- SILANE -- therefor.

Title page,
Item [57], ABSTRACT, delete "siloxane" and insert -- silane -- therefor.

Column 1,
Line 53, delete "Siloxane" and insert -- Silane -- therefor.
Lines 10, 58 and 65, delete "siloxane" and insert -- silane -- therefor.
Line 34, delete "siloxane" and insert -- alkoxysilane -- therefor.
Lines 49-50, delete "independently a mono, di,or tri siloxane" and insert -- alkoxysilanes having at least one Si-O-R bond, where R is an organic functional group or hydrogen -- therefor.
Line 52, after "thereof." insert sentence -- When the compounds are bound to a substrate, R represents the substrate. -- therefor.
Line 54, delete "affective" and insert -- effective -- therefor.
Line 65, delete sentence "These siloxane coupling agents as both the free alkoxysilyl and bound to the substrate are referred to herein as siloxanes." and insert -- These silane coupling agents, as the free unhydrolyzed alkoxysilane, hydrolyzed water solutions, and those bound to a substrate are referred to herein as "alkoxysilanes". -- therefor.
Line 67, delete "Siloxanes" and insert -- Silanes -- therefor.

Column 2,
Line 26, after "aryl" insert -- , hydrogen -- therefor.
Lines 29, 32, 59 and 61, delete "siloxane" and insert -- silane -- therefor.
Lines 66-67, delete "independently a mono, di,or tri siloxane" and insert -- are free alkoxysilanes or bound to a substrate as described previously -- therefor.

Column 3,
Line 3, delete "siloxane" and insert -- alkoxysilane -- therefor.

Column 4,
Lines 3, 11 and 24, delete "siloxane" and insert -- alkoxysilane -- therefor.

Column 5,
Lines 40, 53, 54 and 62, delete "siloxane" and insert -- alkoxysilane -- therefor.
Line 44, after "aryl moieties" insert -- , and heteroatom containing elements, such as ethers -- therefor.
Lines 52 and 56, delete "siloxane" and insert -- silane -- therefor.

UNITED STATES PATENT AND TRADEMARK OFFICE
CERTIFICATE OF CORRECTION

PATENT NO. : 6,489,499 B1
DATED : December 3, 2002
INVENTOR(S) : King et al.

It is certified that error appears in the above-identified patent and that said Letters Patent is hereby corrected as shown below:

Column 6,
Lines 58, 60 and 63, delete "siloxane" and insert -- alkoxysilane -- therefor.

Column 7,
Lines 12, 28, 45 and 49, delete "siloxane" and insert -- silane -- therefor.
Line 66, delete "siloxane" and insert -- trimethoxysilane -- therefor.
Line 67, delete "siloxane" and insert -- alkoxysilane -- therefor.

Column 8,
Lines 5, 21 and 55, delete "siloxane" and insert -- alkoxysilane -- therefor.
Lines 29-30 and 49, delete "siloxane" and insert -- silane -- therefor.
Line 37, delete "siloxane" and insert -- trimethoxysilane -- therefor.

Signed and Sealed this

Twenty-fourth Day of August, 2004

JON W. DUDAS
*Director of the United States Patent and Trademark Office*